United States Patent [19]

Lentsch et al.

[11] 4,376,787
[45] Mar. 15, 1983

[54] CONTROL OF MASTITIS

[75] Inventors: Steven E. Lentsch; William Schmidt, both of Saint Paul, Minn.

[73] Assignee: Economics Laboratory, Inc., Saint Paul, Minn.

[21] Appl. No.: 99,735

[22] Filed: Dec. 3, 1979

[51] Int. Cl.³ .............. A61K 31/185; A61K 31/255; A61K 31/66

[52] U.S. Cl. .................. 424/315; 424/225; 424/224; 424/223; 424/303

[58] Field of Search .............. 424/303, 315, 225, 224, 424/223; 252/DIG. 5

[56] References Cited

U.S. PATENT DOCUMENTS

| | | | |
|---|---|---|---|
| 1,691,228 | 11/1928 | Daimler | 424/303 |
| 2,904,468 | 9/1959 | Davis et al. | 424/315 |
| 3,141,821 | 7/1964 | Compeau | 424/65 |
| 3,337,599 | 8/1967 | Dunbar | 424/303 |
| 3,538,138 | 11/1970 | Dunbar | 424/303 |
| 3,873,591 | 3/1975 | Smith et al. | 424/303 |
| 3,912,767 | 10/1975 | Marisco | 424/303 |
| 3,962,150 | 6/1976 | Viola | 252/546 |
| 4,207,198 | 6/1980 | Kenkare | 252/117 |

FOREIGN PATENT DOCUMENTS

| | | |
|---|---|---|
| 2594 | 6/1979 | European Pat. Off. |
| 363653 | 12/1931 | United Kingdom |
| 464330 | 4/1937 | United Kingdom |
| 759199 | 10/1956 | United Kingdom |
| 792175 | 3/1958 | United Kingdom |
| 1004442 | 9/1965 | United Kingdom |
| 1010200 | 11/1965 | United Kingdom |
| 1069356 | 5/1967 | United Kingdom |
| 1106945 | 3/1968 | United Kingdom |
| 1247804 | 9/1971 | United Kingdom |
| 1304682 | 1/1973 | United Kingdom |
| 1386875 | 3/1975 | United Kingdom |
| 1525441 | 9/1978 | United Kingdom |

OTHER PUBLICATIONS

Barnum et al.—Can. Vet. J., vol. 23, (1982), pp. 50–54.
Bennett–Dairy & Food Sanitation, vol. 2, No. 3, (1982), pp. 110–114.
Fed. Register, vol. 43, No. 4, Jan. 6, 1978.
Updegraff—J. Am. Oil Chem. Soc., vol. 44, Aug. 1967, pp. 481–483.
Cade–Am. Soc. Test. Mat. Sp. Tech. Pub., No. 115, (1952), pp. 33–39.
The Merck Veterinary Manual-4th Edition, (1973), pp. 808–811.
Wilczek et al.—Chem. Abst., vol. 80, (1974), p. 16780S.
Peacock et al.—Chem. Abst., vol. 77, (1972), p. 130633j.
Lickfeld–Chem. Abst., vol. 71, (1969), pp. 28, 129p.

*Primary Examiner*—Sam Rosen
*Attorney, Agent, or Firm*—Merchant, Gould, Smith, Edell, Welter & Schmidt

[57] ABSTRACT

A mastitis controlling method and composition based upon anionic surfactants of the formula $$R-AO_x^-M^+$$

which generally includes organic sulfonates, sulfonic acids, phosphonates and phosphates, the composition being maintained in a pH range of 2.0 to 5.0 (preferably 2.1 to 4.0, and most preferably 2.5 to 3.5). Rapid kill of mastitis-causing gram positive and gram negative microorganisms is achieved in the practice of the instant method.

28 Claims, No Drawings

CONTROL OF MASTITIS

BACKGROUND OF THE INVENTION

Milking of cows on a large scale is almost entirely done with a milking machine. The milking machine draws the milk from the cow's udder by pulsating vacuum, e.g., by attaching a teat cup connected to a vacuum pump and pulsating the vacuum to alternately allow the milk to fill and drain from the area of the udder and teat to simulate hand milking of the cow. The tendency is to minimize the milking time by using high vacuum which can cause irritation or damage to the teat and udder.

The damage to tissue caused by the milking machine followed by exposure of the damaged tissue to certain microorganisms can result in an infection known as mastitis. Control of mastitis is of great economic importance to dairy farmers because an infected cow's contaminated milk cannot be marketed. The udder and teats of an infected cow can be treated with an antibiotic to inhibit the growth of mastitis once it has begun. However, the milk from such cows cannot be sold until the antibiotic is absent from the milk (usually about 3–5 days after the last treatment).

According to experts, prevention of mastitis by the dipping of teats in an antimicrobial (biostatic or biocidal) solution after mixing is one of the most effective procedures that a dairy farmer can follow. An essential function of a teat dip is to prevent mastitis by killing or controlling infectious microorganisms. The teat dip product desirably has a wide spectrum of antibacterial activity (i.e., it can kill or inhibit the growth of a wide variety of mastitis-causing microorganisms), and has emollient properties to prevent irritation of the skin on which it is applied.

PRIOR ART

A number of teat dip products or mastitis control agents are available to dairy farmers which have varying degrees of effectiveness. These products or agents have in common an antimicrobial agent which is an active ingredient (usually the principal active ingredient) of the treating solution.

The following references are believed to be illustrative of published scientific and patent literature regarding teat dips:

British Pat. No. 1,144,637 (Kilco Chemicals Ltd.), published Mar. 5, 1969
U.S. Pat. No. 3,993,777, issued Nov. 23, 1976
U.S. Pat. No. 4,025,628, issued May 24, 1977
"Modern Teat Dips", appearing in *The Veterinary Record*, Vol. 93 (No. 133), Dec. 15, 1973
Philpot et al, *J. Dairy Science*, 58(a):209

As will be apparent from these references, numerous antimicrobial agents have been investigated, including iodophors, PVP-iodine (a particular iodophor), hypochlorites, chlorine dioxide, chlorinated isocyanurates (chlorinated-S-triazene-trione), bromine, hydroxyquinone, ammonium chloride, chlorhexidine, hexachlorophene, diaphene, cetyl pyridinium chloride, and the quaternary ammonium germicides disclosed in the aforementioned U.S. Pat. No. 3,993,777. Of the topically applied antimicrobial agents (i.e., those agents applied directly to the skin) which have been investigated for control of bovine mastitis, iodophors, quaternary ammonium compounds, and chlorine-releasing agents (particularly sodium hypochlorite and, more recently, chlorinated isocyanurates) appear to have gained the widest acceptance among dairy farmers, despite the fact that some of the chlorine-releasing sanitizers (e.g. 4% aqueous NaOCl) can have an irritating effect upon cow teats. (The irritation can be mitigated with emollients but may still occur.) Further, at this stage of commercial development of the iodophors, there is some concern on the part of researchers who believe that this antimicrobial agent may be capable of contaminating the milk. Teat dips of the instant invention are iodine-free.

It is known in the art that linear alkylbenzene sulfonates, or linear alkylbenzene sulfonic acids, (hereafter sometimes collectively referred to as "LAS") are moderately effective bactericides, particularly in mildly acidic media. However, the art teaches that linear alkylbenzene sulfonic acids are generally more active against gram positive organisms such as *Staphylococcus aureus* than against gram negative organisms, particularly at "skin" pH, i.e., greater than 5.0. These microorganisms may have as their origin, water, soil, improperly cleaned utensils, manure, infected cows, human hands, etc. For the most part, gram positive organisms such as *Staphylococcus aureus* originate in mammals (including humans), while many gram negative organisms are found in the feces of animals as well as humans. "Gram positive" and "gram negative" are designations of bacteria which are well-known to one skilled in the art.

In the control of bovine mastitis, rapid killing of bacteria is essential, since prolonged treatment (e.g. more than 15 minutes or even more than a minute) with the teat dip is normally impractical. Bactericidal tests of teat dip formulas are most informative when they are conducted with a view toward measuring their short-term kill. As discussed below, the method and composition of the present invention do provide this desirable rapid kill.

SUMMARY OF THE INVENTION

It has now been discovered that the antimicrobial activity (e.g., biostatic and biocidal activity) against both gram positive and gram negative microorganisms (e.g., mastitis) of an aqueous anionic surfactant is significantly increased when the aqueous mixture has therein a pH maintaining agent (e.g., a buffer) which maintains the pH of the solution on the relatively acidic side, e.g., in the range of 2.0 to 5.0. The anionic surfactants of the present invention have the structure $$R-AO_x^- M^+ \tag{I}$$

wherein R is essentially organic, typically aromatic or aliphatic radical (including alkyl-aryl radicals), A is selected from the group consisting of sulfur or phosphorus, x is 3 or 4, and M is a topically acceptable cation such as a proton, an alkali metal cation, ammonium, or organic ammonium (e.g., triethanolammonium), an alkali metal cation or a proton or mixtures thereof being preferred. The preferred aromatic or aliphatic radicals (the "R" in formula I) are the linear alkyls and linear alkyl-aryls with A being sulfur, and x=3, and M being Na+. One of ordinary skill in this art will recognize the $-AO_x^- M^+$ structure as that characteristic of sulfonic acids, sulfonates, phosphonic acids or phosphonates. This structure necessarily includes linkages of the sort R—O—A or R—A. An aqueous solution of these materials maintained at a pH preferably in the range of 2.1 to 4.0, and most preferably 2.5 to 3.5 has been found to have optimum antimicrobial activity (and hence optimum mastitis inhibition) with tolerable, little or no irritation of the skin.

Accordingly, this invention contemplates a topically applied composition for the killing of mastitis which comprises an aqueous anionic surfactant of structure I maintained at a pH in the range of 2.0 to 5.0, preferably in the range of 2.1 to 4.0 and most preferably in the range of 2.5 to 3.5. "Killing" as the term is used herein is meant to include actual killing as well as inhibition or abatement of microorganism growth. Topical application of the teat dip is preferred, and conventional teat dip ingredients can be such as emollients and water thickeners or thixotropes. Such conventional ingredients are added to impart desirable handling characteristics thereto.

Topical mastitis-treating compositions of this invention, according to available test results, have excellent bactericidal properties against gram negative organisms such as *Pseudomonas aeruginosa, Escherichia coli* (E. coli), *Enterobacter aerogenese, Klebsiella pneumoniae* and appear to provide relative quick bactericidal action, e.g. an effective kill in 15 to 30 seconds. Furthermore, maintenance of compositions in the preferred and most preferred pH ranges appears to provide especially good bactericidal activity against gram negative organisms while not excessively irritating the bovine teat.

COMPONENTS USED IN THE COMPOSITIONS OF THIS INVENTION

As noted previously, compositions of this invention are typically "teat dips" and will be described as such, though, of course, other methods of topical applications besides teat-dipping might be used, if equally effective in killing bacteria. The anionic surfactants, buffers, emollients, and thickeners of a typical teat dip will now be described in detail.

ANIONIC SURFACTANTS

Anionic surfactants useful in the present invention have maximum biocidal activity and/or biostatis against mastitis-causing organisms at a pH in the range of 2.0 to 5.0 (preferably about 2.1 to 4.0 and most preferably in the range of 2.5 to 3.5). Hence, these surfactants are generally present in the present compositions in the ionized form preferably to the extent of 0.5% to 10% by weight.

Anionic surfactants for use in the practice of the present have the formula $$R\text{---}AO_x^-M^+$$

wherein R is essentially organic, typically an aromatic or aliphatic radical (including alkyl-aryl radicals), A is sulfur or phosphorus, x is 3 or 4, and M is a topically acceptable cation (or cations) such as a proton, an alkali metal cation, ammonium, or organic ammonium (e.g., triethanolammonium), an alkali metal cation or a proton being preferred. "Essentially organic" as the term is used herein means primarily hydrocarbon in nature. "Topically acceptable cation" as the term is used herein means non-toxic cation or cation which is acceptable for the topical application intended. R may be two monovalent organic moieties, $R_1$ and $R_2$ in which instance x would be 3 or less. The preferred aromatic or aliphatic radicals (which if sufficiently organic may have inorganic character, e.g. a second—$AO_xM$ structure such as in the sodium salt of sulfonated diphenyl oxide) are the linear alkyls and linear alkyl-aryls. Linear alkylbenzene sulfonates are a particularly preferred class of anionic surfactants which appear to provide unexpected activity against both gram positive microorganisms (e.g., *S. aureus*) as well as gram negative microorganisms (e.g., *Pseudomonas aeruginosa*) in the indicated pH ranges. In the preferred anionic sufactants, R would be an alkyl-aryl radical of preferably the structure

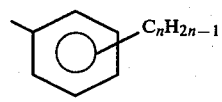

A is sulfur, x is 3 and M is usually a sodium ion.

With respect to the linear alkyl chain of the LAS (i.e., the value of "n" above), it should not be so long as to create incompatibility with water yet not so short so as to reduce antimicrobial action. Therefore, the alkyl chains should preferably be 9 to 18 carbon atoms in length. All sulfonates are not equally effective, the most preferred linear alkyl benzene sulfonic acid salt for use in connection with compositions of the present invention being sodium wherein $R_3$ is organic, (generally alkyl having 12 or fewer carbon atoms), and n has a value of about 1 to 10, $R_3$ is preferably alkyl-aryl having an alkyl chain of 6 to 10 carbon atoms attached to an aromatic nucleus such as benzene.

BUFFERING AGENTS

As discussed below, the composition according to the present invention is most suitable for use as a teat dip when in the form of an aqueous solution containing a major amount of thickened water. Even if neutral, softened, distilled, or deionized water is used, adjustment of the pH of teat dip to the desired range and stabilization of the adjusted pH with a buffer are necessary. The pH of aqueous solutions of compositions according to the present invention should be in the range of 2 to 5, more preferably 2.1 to 4.0 and most preferably in the range of 2.5 to 3.5. A buffer system found to be suitable for maintaining the pH at the desired value (e.g. within about a pH unit) is a citrate-citric acid buffer. Other buffer systems can be used, however, the main requirement dodecylbenzenesulfonate. As is known in the art, the $C_{12}$ benzene sulfonates and the corresponding sulfonic acid are commercially available as mixtures with the $C_{14}$ and $C_{16}$ homologs and sometimes other homologs as well. The degree of purity of the $C_{12}$ species does not appear to be important in the context of this invention, and commercially available forms of the sulfonic acid and its salts are fairly useful, without further purification. Other potentially useful sulfur-based anionic surfactants include sulfonated oleic acid alkylsulfosuccinates, and sodium-N-methyl-N-tall oil taurate.

Although not preferred, the present invention contemplates the use of phosphorus-based anionic surfactants. For example, mono and diphosphate esters of the formula

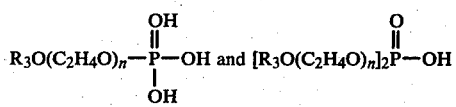

for the buffering agent used being that it be physiologically compatible with the skin, compatible with the other ingredients of the composition, and not detrimental with respect to the antibacterial efficacy of the composition. The citrate of the citric acid buffer is preferably the salt of a monovalent metal base such as an alkali metal hydroxide. To raise the pH to the desired range it may be necessary for a base, e.g., 50% aqueous NaOH, to be added.

As noted above, the presently preferred pH is in the range of about 2.0 to 5.0 (determined at 20° C.). Efficacy roughly comparable to commercially available iodophor teat dips has been observed at this range of pH. Compositions buffered to the preferred and to the most preferred pH ranges exhibit even greater antimicrobial activity.

EMOLLIENTS

Emollients incorporated into compositions of the present invention can serve to assist in forming a protective coating on the skin to retain moisture. To be useful in the present invention, an emollient should have a soothing action on teat skin, should be compatable with aqueous buffered solutions of anionic surfactants, and should not significantly detract from the antimicrobial action of the anionic surfactants utilized in this invention. Liquid organic emollients (e.g. polyols with relatively high boiling points, typically above 100° C. at 1 atmosphere) are preferred, but water soluble or water dispersible solids such as polyvinyl pyrrolidone or sorbitol have been used effectively in known teat dip formulas. Sorbitol takes up moisture under some conditions and is thus believed to provide an emollient action similar to liquid polyols. In addition to polyvinyl pyrrolidone (PVP) and the emollients can be found at column 2, lines 30–43 of the patent to Caughman et al, U.S. Pat. No. 3,933,777, issued Nov. 23, 1976, the disclosure of which is incorporated by reference. All emollients do not work with equal effectiveness, and a preferred emollient for use in practicing the present invention is glycerine. The amount of the emollient in a composition suitable for use, as is, for teat dipping should be in the range of from 0.2 to 20%, most preferably about 12% by weight of the total composition (including aqueous diluent). Amounts up to about 30% by weight of emollient can be used (see U.S. Pat. No. 4,025,628, Table I) but such amounts are not necessary in the context of this invention.

THE AQUEOUS DILUENT

Water is suitable as a diluent in compositions of this invention, because of its unquestionable economic advantages over other liquid diluents. The preferred aqueous diluent used in this invention is water thickened with a thickening agent or thixotropes. One of ordinary skill in this art will be aware of the fact that, the pH of tap water can vary with hardness and other factors. Hard water with a pH approaching 10 is known, as is water with a pH on the slightly acid side. Softened, deionized, distilled, or neutral water is preferred for use in this invention, although a well-designed buffer system can take care of fluctuations in pH which might be introduced by slightly alkaline tap water.

WATER THICKENING AGENTS OR THIXOTROPES

As is well known in the art, a variety of organic and inorganic agents can increase the viscosity, apparent viscosity, or shear-dependent viscosity (thixotropy) of water. Inorganic types include clays such as bentonite, fumed silica, and the like. If desired, clays can be treated with organic coatings. Typical of the organic thickeners are a variety of cellulosic/compounds, e.g. (including modified cellulosic) hydrophilic cellulosic esters and ethers. Other typical known thickening agents for water are disclosed at column 3, lines 19–40 of the Caughman et al patent (3,993,777), the disclosure of which is hereby incorporated by reference. All thickeners do not work with equal effectiveness in this invention, the preferred ones being the cellulosic type, e.g. sodium carboxymethyl cellulose (CMC). A fraction of a percent by weight of such thickeners can increase the viscosity measurement to more than several hundred centipoise. A few percent can thicken water to several thousand centipoise. An important aspect of this thickening is that the teat dip formula is fluid enough for pouring or dipping but still has sufficient thixotropy or viscosity to resist rapid draining or running off from the teat or udder. More than 0.1% by weight of thickener (based on the total composition) provides a thickening effect, while 20 weight-% or more may cause too much thickening. Optimum results are provided with about one to two parts by weight of thickener to each 50–100 parts of water in the composition.

OTHER INGREDIENTS

As is known in the art of bactericidal compositions, colorants (e.g. dyes or pigments), odorants, extenders, diluents, and other non-essential or optional ingredients can be included in teat dip formulas and this can be utilized (if desired) in compositions of this invention. Colorants are particularly desirable for aesthetic reasons and are also added for convenience in identifying a product from among a number of products which a dairy farmer may have in the milk-house.

Compositions according to the present invention have been found to be particularly effective when used as a teat dip, though spraying or swabbing onto the teats might be expected to have somewhat similar bactericidal effects if the contact time is about the same. Preferably, the teats of the animal are dipped in a reservoir or receptacle containing a thickened aqueous teat dip of the present invention with the excess being then allowed to drip freely when the source is removed. The high viscosity of the teat dip (especially when an optional thixotrope such as sodium carboxy-methyl-cellulose is added) ensures a contact time greater than a second, e.g. 15 seconds to 15 minutes.

EXAMPLES 1–14

In accordance with the present invention, four antimicrobial formulations (Examples 1 through 4) were made up to different final pH's. These examples had essentially the same level of LAS, emollient, water and thixotrope. The formulas of the Examples 1-4 are set forth below in percent by weight:

| Number | Ingredient | Ex 1 | Ex 2 | Ex 3 | Ex 4 |
|---|---|---|---|---|---|
| 1 | linear alkyl benzene sulfonate[a] | 2.00 | 2.00 | 2.00 | 2.00 |
| 2 | sodium carboxymethyl-cellulose | 1.50 | 1.50 | 1.50 | 1.50 |
| 3 | glycerine[b] | 8.00 | 8.00 | 8.00 | 8.00 |
| 4 | citric acid[c] | 0.400 | 0.400 | 0.400 | 0.400 |

-continued

| Number | Ingredient | Ex 1 | Ex 2 | Ex 3 | Ex 4 |
|---|---|---|---|---|---|
| 5 | NaOH[d] | 0.062 | 0.292 | 0.513 | 0.668 |
| 6 | color (F, D and C No. 1) | 0.014 | 0.014 | 0.014 | 0.014 |
| 7 | Water | to 100% | to 100% | to 100% | to 100% |
| | Final pH | 2.00 | 3.05 | 4.00 | 5.00 |

Notes
[a] sodium dodecylbenzene sulfonate
[b] USP 96%
[c] aqueous 50% by weight aqueous solution
[d] 50% by weight aqueous solution The samples were prepared by first dispersing the carboxymethyl cellulose in the water with vigorous stirring and subsequently adding (in the following order) components 1, 3, 4, 5 and 6 while avoiding excess foam formation.

Each of the Ex 1–4 compositions were evaluated for their microbiological activity against *Staphylococcus aureus*, *E. coli*, *Klebsiella pneumoniae*, *Pseudomonas aeruginosa*. This evaluation procedure was generally according to the Association of Analytical Chemists' (AOAC) Methods of Analysis (12th Edition 1975), Germicidal and Detergent Sanitizer Test, Official Action. In this method, ninety nine milliliters of the composition to be tested were inoculated (by means of a 1 ml pipette) with a liquid culture suspension of the test organism, the initial inoculum per ml of the culture having been previously determined. After 30 seconds, a second 1 ml aliquot of the inoculated test material was removed (by pipette), neutralized (to "quench" the composition's killing action) and a plate count was taken to determine the number of surviving organisms.

The results are summarized in Table I.

TABLE 1

AOAC GERMICIDAL & DETERGENT SANITIZER TEST

| FORMU-LATION | TEST ORGANISM | NUMBER OF SURVIVING ORGANISMS/EXPOSURE TIME | | | |
|---|---|---|---|---|---|
| | | 30 sec. | 1 min. | 5 min. | 15 min. |
| pH 2 | Staph a. | 0 | 0 | 0 | 0 |
| | E. coli | 0 | 0 | 0 | 0 |
| | Klebsiella p. | 0 | 0 | 0 | 0 |
| | Ps. a | 0 | 0 | 0 | 0 |
| pH 3 | Staph a. | 0 | 0 | 0 | 0 |
| | E. coli | 0 | 0 | 0 | 0 |
| | Klebsiella p. | 0 | 0 | 0 | 0 |
| | Ps. a | 0 | 0 | 0 | 0 |
| pH 4 | Staph a. | 0 | 0 | 0 | 0 |
| | E. coli | $>10^7$ | $>10^7$ | $>10^6$ | $1 \times 10^6$ |
| | Klebsiella p. | $>10^7$ | $>10^7$ | $>10^6$ | $>10^5$ |
| | Ps. a | $7 \times 10^5$ | $1 \times 10^4$ | 0 | 0 |
| pH 5 | Staph a. | $4 \times 10^2$ | 0 | 0 | 0 |
| | E. coli | $>10^7$ | $>10^7$ | $>10^7$ | $-10^7$ |
| | Klebsiella p. | $>10^7$ | $>10^7$ | $>10^7$ | $>10^7$ |
| | Ps. a | $>10^7$ | $>10^7$ | $>10^7$ | $>10^7$ |

| Initial inoculum, cells 1 ml of test product | |
|---|---|
| Staphylococcus aureus | $1.3 \times 10^8$ |
| E. coli | $9.6 \times 10^8$ |
| Klebsiella pneumoniae | $2.0 \times 10^8$ |
| Pseudomonas aeruginosa | $5.0 \times 10^8$ |

Table 1 clearly indicates the increased activity of the compositions of the present invention against both gram positive and gram negative organisms as pH is dropped.

EXAMPLE 5

According to the procedure of Example 1, an antimicrobial composition of the following formula was prepared.

| Ingredient | % by weight |
|---|---|
| sodium dodecylbenzene sulfonate[a] | 2.00 |
| sodium carboxymethyl-cellulose | 1.50 |
| glycerine[b] | 12.00 |
| citric acid[c] | 0.80 |
| NaOH[d] | 0.30 |
| color (F, D and C, No 1) | 0.0054 |
| water | to 100% |
| Measured final pH | 3.00 |

Notes:
[a] sodium dodecylbenzene sulfonate
[b] USP 96%
[c] aqueous 50% by weight aqueous solution
[d] 50% by weight aqueous solution

EXAMPLE 6

The composition of Example 5 (i.e., a pH=3 composition) was tested for its microbiocidal activity against the gram positive and gram negative organisms indicated in Table 2. The composition was tested generally according to the AOAC method discussed in Examples 1–4. As indicated in Table 2, the composition of Example 5 killed essentially all of the listed organisms, i.e., the tested composition gave a 100% reduction in the number of test organisms in less than 30 seconds.

TABLE 2

| TEST ORGANISM | Initial inoculum per ml of product | Exposure period | No. of surviving organisms | % Reduction |
|---|---|---|---|---|
| Staphylococcus aureus | $2 \times 10^8$ | 30 sec. | 0 | 100 |
| Streptococcus agalactiae | $6 \times 10^4$ | 30 sec. | 0 | 100 |
| Streptococcus dysgalactiae | $1 \times 10^7$ | 30 sec. | 0 | 100 |
| Streptococcus uberis | $9 \times 10^4$ | 30 sec. | 0 | 100 |
| Escherichia coli | $8.7 \times 10^7$ | 30 sec. | 0 | 100 |
| Enterobacter aerogenese | $8.5 \times 10^7$ | 30 sec. | 0 | 100 |
| Klebsiella pneumoniae | $2 \times 10^7$ | 30 sec. | 0 | 100 |
| Pseudomonas aeruginosa | $6 \times 10^7$ | 30 sec. | 0 | 100 |

EXAMPLE 7

The composition of Example 5 was tested for its antimicrobial activity under conditions of an organic load. In this test, the method of Example 6 was employed with the exception that 10% by volume whole milk was mixed with the Example 5 composition. Normally, such an organic load would be expected to reduce the antimicrobial activity of the composition against a given organism in the 30 second time exposure period. No such reduction in activity was found, the addition of the milk organic load producing essentially no change from the results shown in Table II.

EXAMPLE 8

The composition prepared in Example 5 was applied to abraded and intact areas of the shaved backs of live test rabbits. The material was kept in contact with the rabbits' skin for a period of 24 hours and when wiped (not washed) without further irritating the skin. In accordance with the Federal Hazardous Substances Act (FHSA) and associated regulations the Example 5 material was *not* found to be a primary skin irritant. Further studies also indicated the composition was not a primary eye irritant as defined by FHSA.

What is claimed is:

1. A method for killing mastitis-causing gram negative organisms including *Pseudomonas aeruginosa, Escherichia coli,* or *Klebsiella pneumoniae* or gram positive organisms including *Staphylococcus auereus* on an animal's teats comprising the step of treating the teats of the animal with an thickened aqueous medium formulated to ensure a contact time between the teats and the medium of 15 seconds to 15 minutes, the medium comprising:

(a) anionic surfactant of the formula $$RAO_x^- M^+$$

wherein R is essentially organic, A is sulfur or phosphorus, x is 3 or 4, and M is topically acceptable cation; and (b) a pH modifying or maintaining substance in an amount sufficient to adjust a pH of the composition to a value in the range of 2.0 to 5.0.

2. A method according to claim 1 wherein the R of the anionic surfactant is an alkyl-aryl radical.

3. A method according to claim 1 wherein the R of the anionic surfactant is linear alkyl-aryl radical.

4. A method according to claim 1 wherein R of the anionic surfactant is linear alkylbenzene radical.

5. A method according to claim 1 wherein A of the anionic surfactant is sulfur.

6. A method in accordance with claim 5 wherein x is 3.

7. A method in accordance with claim 5 wherein R is linear alkylbenzene radical.

8. A method in accordance with claim 7 wherein the anionic surfactant is sodium linear alkylbenzene sulfonate.

9. A method in accordance with claim 8 wherein the anionic surfactant is sodium dodecylbenzene sulfonate.

10. A method according to claim 1 wherein the anionic surfactant is lineaar alkylbenzene sulfonate.

11. A method according to claim 1 wherein the anionic surfactant is sodium dodecylbenzene sulfonate.

12. A method according to claim 1 wherein the pH modifying substance modifies the pH to a value in the range of 2.1 to 4.0.

13. A method according to claim 1 wherein the pH modifying substance modifies the pH of the composition in the range of 2.5 to 3.5.

14. A method according to claim 1 in which the pH modifying substance is a buffer.

15. A method according to claim 14 in which the buffer is a mixture of citric acid and sodium citrate.

16. A method according to claim 1 which further comprises a thixotrope.

17. A method according to claim 16 wherein the thixotrope is sodium carboxymethyl cellulose.

18. A method for killing mastitis-causing gram negative organisms including *Pseudomonas aeruginisa, Escherichia coli,* or *Klebsiella pneumoniae* or gram positive organisms including *Staphylococcus aureus* on an animals's teats comprising the step of dipping the teats of the animal in a reservoir containing an thickened aqueous medium formulated to ensure a contact time between the teats and the medium of 15 seconds to 15 minutes, the medium comprising:

(a) anionic surfactant of the formula $$RAO_x^- M^+$$

wherein R is organic, x is 3 or 4, A is sulfur or phosphorus, and M is a topically acceptable cation; and (b) a pH modifying or maintaining substance in an amount sufficient to adjust the pH of the composition to a value in the range of 2.0 to 5.0.

19. A method according to claim 18 wherein R is monovalent, alkyl-aryl radical.

20. A method according to claim 18 wherein R is an alkyl-benzene radical.

21. A method according to claim 18 wherein R is of the structure $$\underset{}{\bigcirc}\!\!-\!C_nH_{2n-1}$$

n having a value of from 9 to 18.

22. A method according to claim 21 wherein the $C_nH_{2n-1}$ structure is linear.

23. A method according to claim 21 wherein the anionic surfactant is sodium dodecylbenzene sulfonate.

24. A method according to claim 18 wherein the pH maintaining substance is a buffer.

25. A method according to claim 24 wherein buffer modifies the composition to a pH in the range of 2.1 to 4.0.

26. A method according to claim 18 wherein the buffer maintains the pH of the medium in the range of 2.5 to 3.5.

27. A method according to claim 18 wherein the mastitis-causing organisms are killed in less than 5 minutes.

28. A method according to claim 18 wherein the mastitis-causing organisms are killed in less than 30 seconds.

* * * * *